(12) United States Patent
Asami et al.

(10) Patent No.: US 6,265,450 B1
(45) Date of Patent: *Jul. 24, 2001

(54) ANTI-STRESS COMPOSITION

(75) Inventors: Sumio Asami, Ibaraki; Zhi-bo Yang, Otsui; Eiji Yamashita, Myozai-gun; Hayao Otoze, Naruto, all of (JP)

(73) Assignees: Suntory Limited, Osaka; Itano Refrigerated Food Co., Ltd., Tokushima, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/740,325

(22) Filed: Oct. 28, 1996

(30) Foreign Application Priority Data

Oct. 26, 1995 (JP) .................................. 7-279225

(51) Int. Cl.$^7$ .................................. A01N 35/00
(52) U.S. Cl. ................ 514/691; 514/725; 568/378; 424/439; 424/456
(58) Field of Search ................ 514/725, 691; 568/378; 424/439, 456

(56) References Cited

FOREIGN PATENT DOCUMENTS

| | | |
|---|---|---|
| 2 534 091 A1 | 2/1976 | (DK) . |
| 0 474 347 A1 | 3/1992 | (EP) . |
| 0 498 824 B1 | 8/1992 | (EP) . |
| 0 547 422 A2 | 6/1993 | (EP) . |
| 0 565 989 A1 | 10/1993 | (EP) . |
| 2 280 110 A | 1/1995 | (GB) . |
| 01186860 | 7/1989 | (JP) . |
| 03083577 | 4/1991 | (JP) . |
| 7 099888 A | 4/1995 | (JP) . |
| 7-099924 A | 4/1995 | (JP) . |
| 7-099925 A | 4/1995 | (JP) . |
| 7-099926 A | 4/1995 | (JP) . |
| 7-099932-A | 4/1995 | (JP) . |
| 7-118226 A | 9/1995 | (JP) . |

OTHER PUBLICATIONS

Chemical Abstracts AN 1995:655252, Takeuchi et al, 1995.
Chemical Abstract AN 1997:207932, Terao, 1995.
Chemical Abstracts AN 1995:869285, Jyonouchi et al, 1995.
Chemical Abstracts AN 1990:465273, Uchiumi et al, Corresponding to JP 0 204 9091, 1990.
H. Jyonouchi et al., *J. Nutrition*, 125(10):2483–2492 (1995).
H. Jyonouchi et al., *Nutr. Cancer*, 21(1):47–58 (1994).
I. Thompson et al., *Aquaculture*, 133(2):91–102 (1995).
U. Kouzou et al., *Patent Abstracts of Japan*, Publication No. JP 204091 (1990).
D. Yukio et al., *Patent Abstracts of Japan*, Publication No. JP 05124958 (1993).
Uchiumi, Kozo et al., "Astaxanthins as antioxidants in Pharmaceuticals," *Chemical Abstracts*, 113:65273n (1990).
Jyonouchi et al, "Studies of Immunomodulating Actions of Carotenoids. II. Astaxanthin Enhances In Vitro Antibody Production to T–Dependent Antigens Without Facilitating Polyclonal B–Cell Activation," *Nutrition and Cancer*, vol. 19, No. 3, pp. 269–280 (1993).
Tanaka et al, "Chemoprevention of mouse urinary bladder carcinogenesis by the naturally occurring carotenoid astaxanthin," *Carcinogenesis*, vol. 15, No. 1, pp. 15–19 (1994).
Kurashige et al, "Inhibition of Oxidative Injury of Biological Membranes by Astaxanthin," *Physiol. Chem. Phys. & Med. NMR*, vol. 22, pp. 27–38 (1990).
Free Radical Research Communications, Volume of Abstracts, 10.5, "Active Oxygen Radical Species as a First Signal Stress" (Jun. 16–20, 1992) (this Abstract summarizes Japanese Patent No. 6–65068, a copy of which is also enclosed).
The Merck Index, Tenth Edition, No. 866. Astaxanthin, p. 124 (1983).

*Primary Examiner*—Jyothsna Venkat
*Assistant Examiner*—Grace C. Hsu
(74) *Attorney, Agent, or Firm*—Burns, Doane, Swecker & Mathis, L.L.P.

(57) ABSTRACT

An anti-stress composition having for its active ingredient astaxanthin and/or its ester. This composition can be in the form of a pharmaceutical, functional food, food or beverage and so forth.

9 Claims, 7 Drawing Sheets

ANTI-STRESS COMPOSITION

This application claims the benefit of priority to Japan Patent application No. 7-279225 filed Oct. 26, 1995.

BACKGROUND OF INVENTION

1. Field of the Invention

The present invention relates to an anti-stress composition comprising astaxanthin and/or its ester, and a food or beverage to which it is added. More specifically, the present invention relates to a composition for preventing or alleviating decreased immunological function, decreased liver function and fatigue caused by stress as well as those medical conditions due to decreased immunological function caused by stress such as cancer metastasis, comprising astaxanthin and/or its ester, and to a food or beverage prepared by adding said composition to a food or beverage material that essentially does not contain astaxanthin and/or its ester.

2. Related Art

Stress is quite prevalent in modern society, and those diseases caused by stress, namely somatic disorders as well as stress disorders such as neurosis and depression, are increasing. Stress disorders and other related disorders are believed to comprise a condition in which stress destroys the ability to maintain homeostasis by the body. Alleviation and treatment of these disorders consists of nosotropic therapy for each symptom and disease.

In addition, drugs such as antianxiety agents and sleeping pills for temporarily alleviating somatic reactions when exposed to stress are considered to be an effective means of dealing with stress. However, there are no known drugs that are able to fundamentally inhibit or reduce stress. Moreover, various relaxation techniques for the mind and body have been proposed as ways of effectively controlling stress so prevent destruction of the body's homeostasis. However, long-term efforts will most likely be required due to personal differences and other factors.

In addition, various drugs and foods have been developed for the purpose of preventing and reducing stress or fatigue. Typical examples of these include sports drinks and tonics. Sports drinks have a rapid moisture absorption rate and are intended to rapidly supplement vitamins, amino acids and minerals lost due to perspiration. They do not prevent or reduce stress and fatigue directly. Tonics, on the other hand, contain extracts from several medical plants in addition to vitamins and amino acids. These are expected to have physiological effects such as central nervous system stimulation, increased blood flow, cardiac effects and activation of endocrine system. However, many of the physiological effects of these natural drugs are based on old legends, and none are known, on a scientific basis, to prevent or reduce stress.

More recently, there have been numerous reports which stated that stress, affliction and numerous mental disorders are all pronounced emotional disorders, indicating research results that show that these disorders are closely linked with decreased immunological function of the body. Although the concept of mental anguish being a cause of illness is itself quite old, only recently has attention been focused on this concept in scientific fields as well. Considerable immunological research has been conducted on the relationship between stress and cancer in particular. However, there are no known specific compounds that inhibit the onset and metastasis of cancer caused by stress.

Astaxanthin is one of secondary carotenoids, and is present in animals such as crustaceans including krill, shrimp and crabs, the muscle and eggs of salmon and trout, and the body surfaces of sea bream, carp and goldfish.

At present, although astaxanthin is used as a color restorer for cultured fish such as sea bream, salmon, trout and yellowtail, recent research has clearly shown that astaxanthin can become provitamin A as well as demonstrate remarkable antioxidative effects. It is thus expected to be used in natural coloring agents, antioxidants, nutritional supplements, cosmetics and pharmaceuticals [Yamashita, E: Food and Development, Vol. 27, No. 3 (Consecutive Volume No. 409), p. 38–40 (1992)]. In addition, Japanese Unexamined Patent Publication No. 63-83017 discloses a sunburn-preventive cosmetic containing astaxanthin, while Japanese Unexamined Patent Publication No. 2-49091 discloses an antioxidant having astaxanthin for its active ingredient along with a pharmaceutical and an antiphlogistic for defending against oxidative tissue disorders of the body.

In addition, astaxanthin is also known to have cancer cell growth inhibitory activity [Carotenoids of Marine Life (Miki, W. ed.), p.105–113, Koseisha, Koseikaku (April 1993)] and antibody production activity [H. Jyonouchi et al., Nutrition and Cancer, Vol. 19, No. 3, p. 269–280 (1993)].

However, astaxanthin is not known to have anti-stress effects or be effective in the prevention or alleviation of decreased immunological function, decreased liver function and fatigue.

SUMMARY OF THE INVENTION

Thus, the present invention is intended to provide a composition, and a food or beverage composed by adding said composition, that has a high degree of safety, and is used for the purpose of preventing or alleviating various symptoms accompanying stress, and particularly decreased immunocompetency, decreased liver function and fatigue caused by stress as well as medical conditions and so forth due to decreased immunological function caused by stress such as cancer metastasis and cancer promotion.

As a result of earnest research conducted to solve the above-mentioned problems, the inventors of the present invention found that astaxanthin and/or its ester has effects that prevent or alleviate various symptoms accompanying stress, and particularly decreased immunological function, decreased liver function and fatigue caused by stress as well as medical conditions and so forth due to decreased immunological function caused by stress such as cancer metastasis, thus leading to completion of the present invention.

Thus, the present invention is intended to provide an anti-stress composition comprising astaxanthin and/or its ester.

In addition, the present invention relates to a pharmaceutical or functional food for preventing or alleviating decreased immunological function, decreased liver function and fatigue caused by stress as well as medical conditions due to decreased immunological function caused by stress such as cancer metastasis and infection, comprising astaxanthin and/or its ester.

Moreover, the present invention is intended to provide a food or beverage in which an anti-stress composition or a composition for preventing or alleviating various symptoms such as decreased immunological function caused by stress is added to a food or beverage that essentially does not contain astaxanthin and/or its ester.

DETAILED DESCRIPTION

Figure 1:
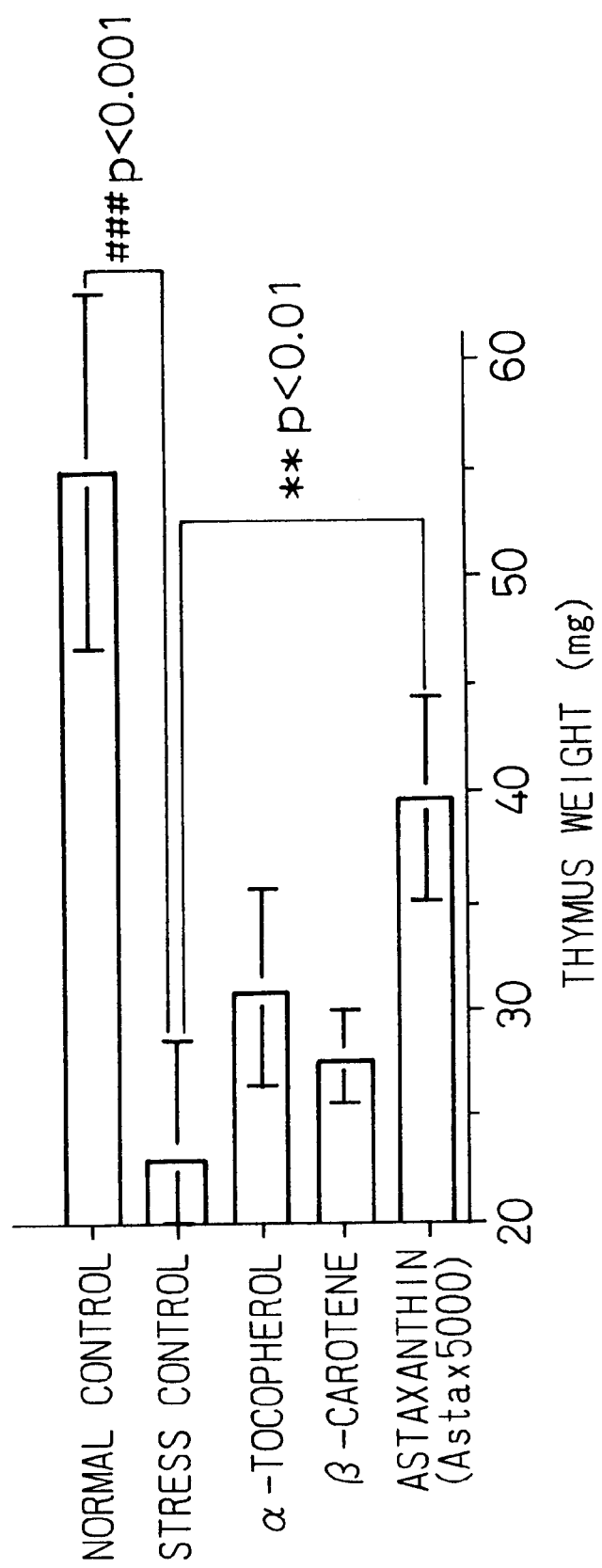
FIG. 1 is a graph showing the weight increasing effect of astaxanthin on decreased thymus weight caused by restraint stress.

Stress refers to a state of distortion within the body, and includes both harmful factors applied from outside the body (stress factors) and a defense reaction that occurs in response to these stress factors. Although stress theory was first advocated by H. Selye, stress factors include physical (cold, radiation, noise, etc.), chemical (drugs, vitamin deficiency, hypoxia, etc.) and biological (bacterial infections, etc.) factors as well as mental factors (scholastic pressure, surgery, athletic competitions, etc.), and include so-called emotional stress.

When the body is subjected to stress factors, a biological response is known to occur mediated by the autonomic nervous system and the endocrine system. In the endocrine system in particular, adrenocorticotropic hormone (ATCH) is secreted from the pituitary gland, causing the secretion of adrenocortical hormones that affect the entire body and result in a series of reactions (general adaptation syndrome).

The first stage is known as the warning reaction stage. This consists of passive disorders or signs of shock along with aggressive defense symptoms in response to this during exposure to stress. The second stage is the resistance stage. The weight of the adrenal cortex increases, and resistance to stress factors reaches its most potent and stable state. However, resistance to other stress factors conversely decreases. The third stage is the exhaustion stage. As stress factors persist for a long time at high levels, the capabilities of the body finally grow tired resulting in a loss of adaptive abilities (Nanzando Publishing, Medical Dictionary, pub. Feb. 1, 1990, 10th edition, p. 41).

Thus, although the stress response plays the useful role of a defense reaction for the body, due to excessive secretion of cortisol and adrenalin during this response, there are harmful effects on numerous body tissues, particularly in the case the body is subjected to loading by excessively high levels of stress. As a result, the body is longer able to maintain homeostasis and various diseases caused by stress are thought to occur as a result of this process. Namely, fatigue occurs due to consumption of large amounts of proteins and lipids in muscle and other tissues due to excessive secretion of cortisol. In addition, the mucous membranes of the stomach and duodenum are destroyed resulting in the occurrence of gastric and duodenal ulcers. In addition, excessive secretion of adrenalin tends to result in hypertension and diseases of the circulatory system.

Moreover, there is also known to be a correlation between stress, immunity and cancer (Imura, Y.: Neuroendocrinimmunology, Asakura Shobo Pub., pp. 299–305, 1993). Namely, although stress affects nearly all neuroendocrine functions, both sympathetic nerves and the adrenal axis, and the hypothalamus and the pituitary axis are affected by stress, bringing about reduced function of the immune system by means of a complicated process. The effect of stress is the result of modification by the nervous system, endocrine system and immune system, and is bidirectional.

Thus, stress is considered to reduce the function of NK cells and cell traumatizing T cells, which play an important role in the immune defense mechanism against cancer, and as a result, is intimately involved in the occurrence and progress of cancer. It has also been clearly shown that bioreaction modifying substances modify the immune system and cause changes in the interaction between the neural, endocrine and immune systems, thereby changing the responsiveness to stress loading. This also suggests the possibility of defending against cancer metastasis. Moreover, infections also tend to occur easily since stress inhibits immunological function.

Astaxanthin and/or its ester, which is the active ingredient of the present invention, has been found in shrimp eggs [Kuhn, et al.: Angew. Chem. 51, 465 (1938) or Ber., 71, 1879 (1938)], in animal organs [Kuhn, et al., Ber., 72, 1688 (1939)], in plants [Tischer, et al.: Z. Physiol. Chem., 267, 281 (1941)], in the petals of Amur adonis and buttercups [Seybold, et al., Nature, 184, 1714 (1959)] and the red wings of birds [Z. Physiol. Chem., 288, 20 (1951)], and its structure has been determined [Grangaud, Comt. Rend., 242, 1767 (1956), or Andrews, et al., Acta. Chem. Scand., B28, 730 (1974)]. Methods for its synthesis have also been established [Cooper, et al., J. Chem. Soc. Perkin Trans. I, 1975, 2195, Kienzle, et al., Helv. Chim. Acta, 61, 2609 (1978), Widmer, et al., Helv. Chim. Acta., 64, 2405 (1981), Mayer, et al., Helv. Chim. Acta., 64, 2419 (1981)], and chemically synthesized products are easily available.

Chemically synthesized astaxanthin, an extract of Phaffia, Tigriops, (red water flea), the shell of a crustacean such as krill, green algae or microalgae containing astaxanthin and/or its ester (which may be in the form of a solvent-extracted extract or that which has been appropriately purified as necessary), or a powder prepared by grinding a crustacean or Haematococcus species green algae containing astaxanthin and/or its ester, can be used for said active ingredient of the present invention.

For example, a method for extracting astaxanthin and/or its ester from the shell of a crustacean using an alkylester carboxylate is described in Japanese Unexamined Patent Publication No. 58-88353, a method for producing astaxanthin and/or its ester by culturing green algae able to biosynthesize astaxanthin, examples of which include Clamvdomonas, Haematococcus, Chlorocytrium, Chlorella, Chlorococcum, Characium, Trebouxia, Dictyosphaerium, Scenedesmus, and Hydrodictycm, in a medium containing Na salt, K salt and Rb salt is described in Japanese Unexamined Patent Publication No. 1-187082, and a method for producing astaxanthin and/or its ester by culturing astaxanthin producing yeast cells such as Phaffia species in Difco YM medium under specified conditions following mutation treatment is described in PCT Japanese National Publication No. 2-504101.

A method for increasing the formation of astaxanthin by *Haematococcus pluvialis* by adjusting the concentration ratio C:N in the culture medium during at the end of the growth phase of the microalgae species is described in PCT Japanese National Publication No. 2-501189, a mutant strain of yeast having the ability to produce astaxanthin in high yield is described in Japanese Unexamined Patent Publication No. 3-206880, and a method for manufacturing astaxanthin at a high level by a mutant strain of *Phaffia rhodzyma* is described in Japanese Unexamined Patent Publication No. 4-228064.

In addition, a method for obtaining a large amount of astaxanthin by inducing cyst formation in algae by a specified method after aerobically culturing said *Haematococcus pluvialis* is disclosed in Japanese Unexamined Patent Publication No. 5-68585, and a method for extracting astaxanthin from Adonis species plants is disclosed in Japanese Published Patent Publication No. 5-509227. In the present invention, an extract containing astaxanthin and/or its ester obtained by any of these methods can be used (including that in the form of a solvent-extract or that which has been appropriately purified as necessary). In addition, that which has been obtained by methods other than those described above can also be used provided it can effectively provide the properties of the active ingredient of the present invention.

Moreover, although an astaxanthin-containing powder obtained by low-temperature drying followed by grinding of a raw crustacean is disclosed in Japanese Unexamined Patent Publication No. 1-186860, while a ground algae composition obtained by Haematococcus species green algae is disclosed in Japanese Unexamined Patent Publication No. 3-83577, any powder containing astaxanthin and/or its ester can also be used in the present invention. In addition, any method other than that indicated above can be suitably used provided it is able to effectively provide the properties of the active ingredient of the present invention.

In addition, although a method for synthesizing astaxanthin by reacting a specific tertiary alcohol and trifluoroacetic acid at low temperatures and without using excessive reagents by going through a novel intermediate is disclosed in Japanese Unexamined Patent Publication No. 4-225933, astaxanthin and/or its ester chemically synthesized by any method, including the above method, can also be used in the present invention.

Moreover, a method for manufacturing yellow to reddish-orange pigment astaxanthin is described in Japanese Unexamined Patent Publication No. 60-4558 wherein the viable form or dried form of krill is immersed in an organic solvent such as acetone, n-hexane or ethyl acetate, the pH of the resulting solvent extract, in which the pigment is eluted, is neutralized, and lipase or base is added to decompose fatty acids and other impurities and create a liquid system followed by super-critical gas extraction, molecular distillation or washing using dilute base.

In addition, a method for manufacturing orange pigment astaxanthin is disclosed in Japanese Unexamined Patent Publication No. 61-281159 wherein, after selectively hydrogenating unsaturated lipids other than the pigment with a catalyst in a crude pigment solution in which dried krill are extracted with an organic solvent such as acetone or n-hexane, lipase is added to hydrolyze the lipid, and the dissociated fatty acid is removed by addition of urea and/or molecular distillation followed, if necessary, by further concentration and purification by column chromatography. Moreover, it is described in Yamashita, E.: Food and Development, Vol. 27, No. 3 (Consecutive Volume No. 409), p. 38–40 (1992) that astaxanthin diester, monoester and free astaxanthin can be separated by performing high-performance liquid chromatography (HPLC) on a organic solvent extract or super-critical extract of krill.

Japanese Unexamined Patent Publication No. 5-155736 describes the elution and recovery of pigment by performing HPLC to remove triglycerides, polar lipids and so forth to dramatically increase pigment concentration, the removal of substances that are the source of the characteristic odor of marine products, the use of, for example, silica gel, silicic acid or activated alumina for the adsorbent that serves as the stationary phase packed into the column, the use of, for example, n-hexane, cyclohexane or petroleum ether for the low polar solvent that serves as the mobile phase, the use of, for example, n-hexane, ethyl acetate or methanol for the polar solvent, and elution of low polar lipids such as triglycerides with n-hexane followed by increasing the content of acetone in the n-hexane (the acetone content being within a range of roughly 0.1–20% acetone/n-hexane) for purification of the pigment.

In the present invention, an extract containing astaxanthin and/or its ester that has been purified with any of the above methods can also be used. In addition, methods other than those above can also be suitably used provided they are able to effectively provide the properties of the active ingredient of the present invention.

Also in the present invention, the previously described crude extracts or powders containing astaxanthin and/or its ester, that which has been suitably purified as necessary, or that which has been chemically synthesized can be used alone or in a suitable combination.

In the present invention, esters of astaxanthin include monoesters or diesters of saturated fatty acids such as palmitic acid and stearic acid, or unsaturated fatty acids such as oleic acid, linoleic acid, α-linolenic acid, γ-linolenic acid, bis-homo-γ-linolenic acid, arachidonic acid, eicosapentaenic acid and docosahexaenic acid, and these esters can be used alone or in a suitable combination. Since the structure of astaxanthin is such that an excess oxo group and a hydroxy group are present in the β-carotene skeleton on both of its ends, the stability of the free molecule is low in comparison with β-carotene. In contrast, that in which the hydroxy groups on both ends are esterified with unsaturated fatty acid and so forth (e.g., krill extract) is more stable.

Although astaxanthin and/or its crude extract can be used directly after being dissolved in ethanol and diluted with water, it can also be prepared into a latex preparation as necessary. In the preparing of a latex preparation, a preparation can be easily prepared by adding gallic acid, L-ascorbic acid (or its ester or salt), gum (e.g., locust bean gum, qua gum or gelatin), vitamin P (e.g., flavoids such as hesperidin, lutin, quercetine, catechin, thianidine and eliodictin or mixtures thereof) to the aqueous phase, or by adding astaxanthin, astaxanthin crude extract or a mixture thereof to the oily phase, and then adding glycerine fatty acid ester or oil, examples of which include vegetable seed oil, soy bean oil, corn oil and other routinely used liquid oils. When emulsifying, a high-speed agitator or homogenizer should be used to mix and emulsify.

The astaxanthin of the present invention is inherently a naturally-occurring substance. Since it has been eaten, it can be easily considered to have low toxicity and a high degree of safety. It also has considerable significance as an anti-stress composition. In actuality, 2 g/kg of ASTAX 1700 (Itano Refrigated Food Co., Ltd., oil containing 1.7% by weight of astaxanthin), an astaxanthin-containing extract obtained from krill shell and purified by HPLC, was given in a single oral administration to 4 week old, male ICR mice to assess its acute toxicity. As a result, there were no abnormalities observed with respect to general condition, appearance, body weight changes and autopsy findings.

The astaxanthin and/or its ester of the present invention can be used in the form of a pharmaceutical, cosmetic, functional food, nutritional supplement and beverage or food.

The composition of the present invention is able to prevent or improve various health disorders caused by stress. Thus, the composition of the present invention can also be used for mental or physical relaxation or for mental stabilization.

In addition, the composition of the present invention is able to prevent or alleviate decreases in immnological function caused by stress, such as physical stress caused by restraint, noise, surgical procedures or burns, disturbances in biological rhythm or social stress, and mental stress such as conditioning and passive avoidance. Thus, the composition of the present invention can be used to prevent or alleviate medical conditions caused by decreased immunological function due to stress, examples of which include infection, cancer metastasis and cancer promotion. Furthermore, improvement of conditions in the present invention includes the treatment of disease.

In addition, the composition of the present invention is able to prevent or alleviate gastric and duodenal ulcers brought about by destruction of mucous membrane in the stomach and duodenum caused by stress, decreased organ function such as that of the liver caused by stress, as well as hypertension and diseases of the circulatory system. Moreover, since the composition of the present invention is also able to inhibit physical stress, mental stress and various symptoms of fatigue caused by both, it can be used before, during and after physical labor, mental work or sports. Furthermore, alleviation of condition in the present invention includes the treatment of disease.

In the case of using the active ingredient of the present invention as a pharmaceutical, it may be administered in any formulation provided oral administration or parenteral administration can be suitably performed, examples of which include injection solutions, parenteral fluid, powders, granules, tablets, capsules, pills, enteric-coated pills, troaches, internal medications, suspensions, emulsions, syrups, external medications, fomentations, nasal drops, ear drops, eye drops, inhalants, ointments, lotions, suppositories and enteral nutrients. They may be used either alone or in combination according to the symptoms. Each of these formulations can be prepared using known adjuvants routinely used in the field of drug preparation technology with the main drug according to the purpose of use in accordance with routine methods, examples of which include vehicles, binders, preservatives, oxidation stabilizers, decomposing agents, lubricants and correctives.

In addition, although the dose varies according to the purpose of administration and status of the patient (sex, age, body weight and so forth), the normal adult dose as astaxanthin in the case of oral administration is 0.1 mg to 10 g per day and preferably 0.1 mg to 1 g per day, while the range for obtaining preventive effects is 0.1 mg to 100 mg per day. In the case of parenteral administration, the normal adult dose is 0.01 mg to 1 g per day and preferably 0.01 mg to 100 mg per day, while the range for obtaining preventive effects is 0.ol mg to 10 mg per day.

In a food or beverage of the present invention prepared by adding the composition of the present invention having for its active ingredient astaxanthin and/or its ester to a food or beverage material essentially not containing astaxanthin and/or its ester, "a food or beverage essentially not containing astaxanthin and/or its ester" is, that in which the total content of astaxanthin and/or its ester daily consumed is less than 0.1 mg since the amount of astaxanthin and/or its ester contained in the finished product is extremely small.

The food or beverage of the present invention can be processed and manufactured by blending the prescribed amount of astaxanthin and/or its ester, or an extract having this, with the food or beverage raw material in accordance with routine methods. Although the blending concentration varies according to the form of the food, generally a concentration of 0.001–10% is preferable, but there are no particular limitations on this concentration. However, it should be prepared so that it contains enough of the active ingredient of the present invention per amount of daily consumption required to demonstrate its anti-stress effect, or demonstrate its effect of preventing or alleviating decreased immunological function, decreased liver function and fatigue caused by stress, or preventing and improving medical conditions due to decreased immunocompetency caused by stress such as cancer metastasis and cancer promotion.

In the food or beverage of the present invention, its form may be a solid or liquid. Examples of such foods include margarine, butter, butter sauce, cheese (natural and processed), cream, shortening, lard, ice cream, yogurt, coffee creamer, dairy products, sauces, soups, meat products, fish products, popcorn, french fries, potato chips, rice seasoning, rolled omelets, Japanese confections (including rice crackers), Western style confections (including pudding, jello, chewy candy, hard candy, drops, caramel, chocolate, chewing gum and pastries), baked confections (including custard, cake, doughnuts, biscuits, cookies and crackers), macaroni, pasta, salad oil, instant soups, dressings, eggs, mayonnaise, fermented bean curd, carbonated beverages, non-carbonated beverages (including fruit drinks and nectar drinks), soft drinks, sports drinks, tea, coffee, cocoa and other non-alcoholic beverages, liqueur, medicinal wine and other alcoholic beverages.

In the case of using the active ingredient of the present invention as a functional food or nutritional supplement, it may be in the form of any of the above-mentioned pharmaceutical preparations including capsules, granules and enteral nutrients. In addition, although examples of processed forms include natural fluid foods, semi-digested nutritional foods, component nutritional foods and drinks that are blended with proteins (although proteins such as milk protein, soy bean protein and egg albumin having a high nutritional value and balanced amino acids are most widely used for the protein source, their degradation products, egg white oligopeptides, soy bean hydrolysis products as well as mixtures of individual amino acids are also used), sugars, fat, trace elements, vitamins, emulsifiers and fragrances, there are no particular limitations on the form provided the form is that of ordinary food products.

In the case of providing in the form of a sports drink or nutritional drink, easily digestible carbohydrates, amino acids, vitamins, minerals and other nutritional additives as well as sweeteners, spices, fragrances and pigments can also be blended in order to provide nutritional balance as well as further improve taste during ingestion.

In addition, the active ingredient of the present application can also be added to any foods when preparing hospital meals under the supervision of a nutritionist based on the instructions of a physician, and meals prepared at the hospital can be given to patients.

Since astaxanthin and/or its ester is insoluble in water, it can be provided in capsules and so forth by suspending in oil either directly or using an emulsifier, astaxanthin and/or its ester can be dissolved in oil, emulsified in an aqueous solution containing surface active agent or polymer and so forth followed by dissolving the resulting emulsion in water, or it can be spray dried and provided in the form of a liquid or powder. Since the solubility of astaxanthin in oil is extremely low, although considerable time is required to dissolve crystals of astaxanthin in oil, the dissolution rate can be increased by using fine crystals. The solubility of astaxanthin also becomes extremely large when heated to 100° C. or above.

On the other hand, esters of astaxanthin are highly soluble in oils, and can be easily dissolved in oils. Examples of such oils include vegetable oils such as soy bean oil, corn oil, rape seed oil, palm oil, olive oil, safflower oil, lemon oil, orange oil, peanut oil and sunflower oil, hardened oils produced by hydrogenating these oils, natural waxes such as lanolin, whale wax and bees wax, animal fats such as beef tallow, pork tallow and butter as well as wheat germ oil and concentrated vitamin E oil. In addition, glycerine fatty acid ester, sucrose fatty acid ester, sorbitan fatty acid ester, soy bean phospholipid, propylene glycol fatty acid ester and stearate diglyceride are used as emulsifiers.

In addition, by enclosing astaxanthin and/or its ester using cyclic dextrin (α-cyclodextrin, β-cyclodextrin and γ-cyclodextrin), a powdered inclusion can be obtained that can be dissolved in water.

Furthermore, since astaxanthin and/or its ester are easily oxidized and decompose relatively easily in air, it is desirable to add an antioxidant such as vitamin E, vitamin C, glutathione, phytinic acid, catechin, flavoids or β-carotene to the active ingredient of the present invention to inhibit its decomposition.

It is desirable to ingest the food or beverage, functional food or nutritional supplement of the present invention in an amount of 0.1 mg to 10 g, and preferably 0.1 mg to 1 g, as astaxanthin for the purpose of preventing and improving symptoms of stress and maintaining health, or 0.1 mg to 100 mg for preventive effects.

EXAMPLES

Although the following Examples provide a detailed explanation of the present invention, the present invention is not limited to these Examples.

Example 1

Effect of Restraint Stress on Decreased Thymus Weight

Six week old, male C57BL/6 mice were purchased from Japan Clea Co., Ltd., and after preliminarily keeping for 1 week in an SPF (specific pathogen free) environment, were used in the experiment at age 7 weeks.

The mice were divided into a restrained group (16 mice) and a non-restrained group (5 mice). The unrestrained group was used as a control group. The restrained group was further divided into 4 groups of 4 mice each, and designated as the restrained control group, vitamin E group, β-carotene group and astaxanthin group. The restrained groups were restrained for 20 hours in metal restraint cages under conditions of minimal body movement and access to drinking water to induce restraint stress.

ASTAX 5000 manufactured by Itano Refrigated Food Co., Ltd. (containing 3.57% astaxanthin diester and 1.53% astaxanthin monoester), extracted and purified from krill, was used for astaxanthin. ASTAX 5000 was dissolved in medium chain fatty acid triglyceride (MCT) to a concentration of 100 mg/10 ml as astaxanthin content and used as the test substance solution. Vitamin E and β-carotene were dissolved in MCT, and MCT only was administered to the control group. The test substances were given orally three times on the day before restraint, immediately after restraint, and on the day after restraint at a dose of 100 mg/kg, for each test substance.

The mice were sacrificed by dislocation of the cervical vertebra 48 hours after the start of restraint. The thymus gland was excised and weighed. Those results are shown in FIG. 1. Thymus weight decreased significantly due to restraint stress loading. The decreased thymus weight is suggesting decreased immunological function. In contrast, this weight decrease was significantly inhibited by administration of astaxanthin, thus confirming its stress inhibitory effect.

Example 2

Figure 2:
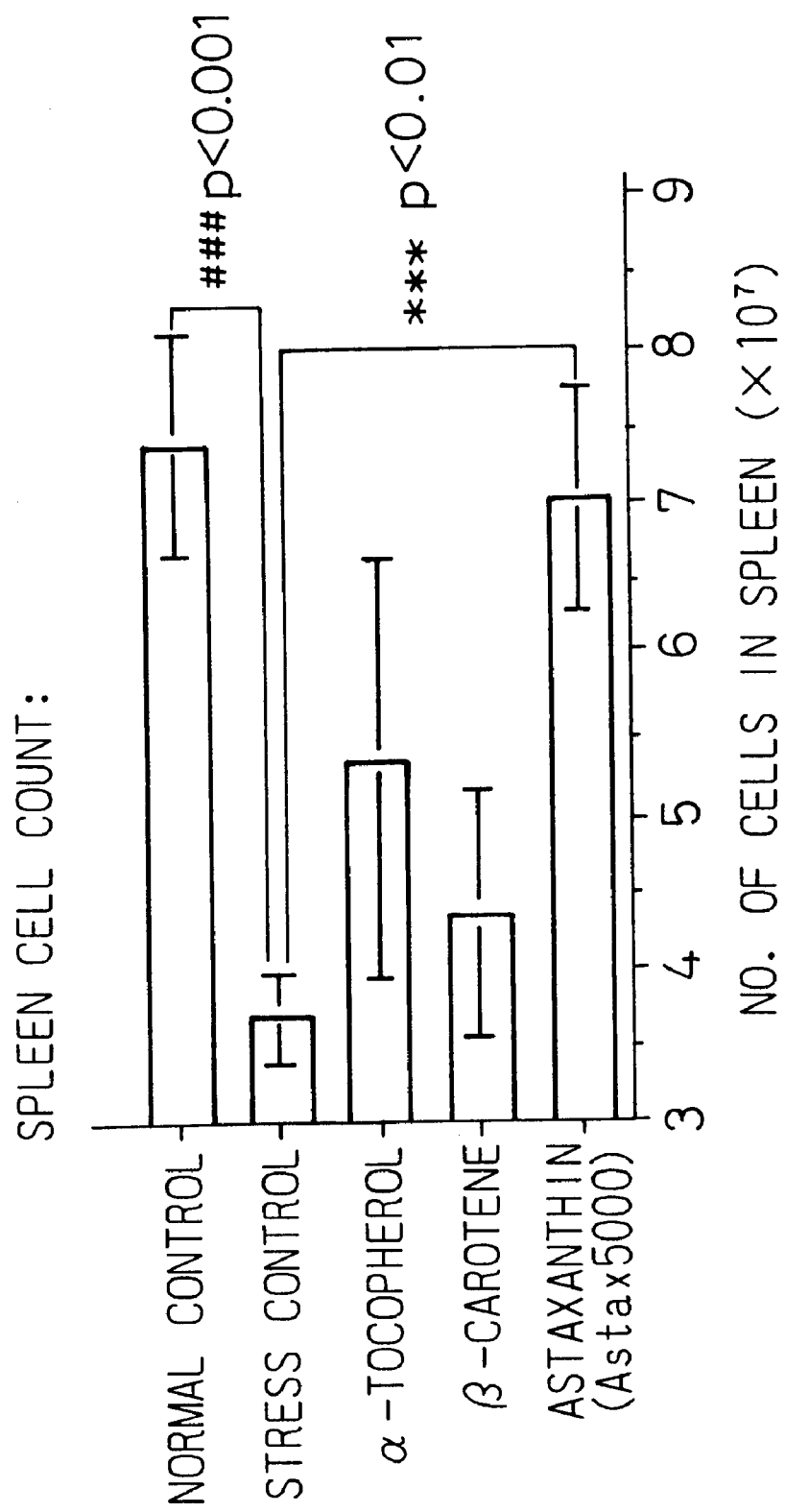
FIG. 2 is a graph showing the improving effect of astaxanthin on decreased lymphocyte number caused by stress.

Effect of Restraint Stress on Reduced Spleen Lymshocvte Count and Decreased NK Cell Activity The spleens were excised from those mice sacrificed after 48 hours after the start of restraint of Example 1. The spleens were then finely sliced with a loose-fitting glass homogenizer to prepare a free cell suspension. The cells were then subjected to hypotonic treatment to remove erythrocytes. After washing, the cells were suspended in RPMI 1640 medium containing 10% fetal calf serum (FCS), and the number of lymphocytes per spleen was counted. Those results are shown in FIG. 2. Although spleen lymphocyte count significantly decreased due to stress loading, administration of astaxanthin was confirmed to significantly inhibit this decrease in lymphocyte count.

Next, the NK cell activity of the above-mentioned spleen lymphocytes was calculated according to the method described below.

Namely, $2 \times 10^6$, $1 \times 10^6$ and $5 \times 10^5$ cells/well of spleen lymphocytes were allocated to each well of a 96-well round-bottom microplate followed by the addition of $1 \times 10^4$ cells/well of YAC-1 target cells labeled with $^{51}Cr$ sodium chromate. After incubating for 6 hours at 37° C., the radioactivity released in 0.1 ml of supernatant was measured to evaluate cell impairment. NK cell activity was determined as the number of cells impairing the target cells by 30% ($LU_{30}$) using the following equation.

$$\% \text{ Cytolysis} = (\text{Experimental cpm} - \text{Spontaneous cpm})/(\text{Maximum cpm} - \text{Spontaneous cpm}) \times 100$$

Figure 3:
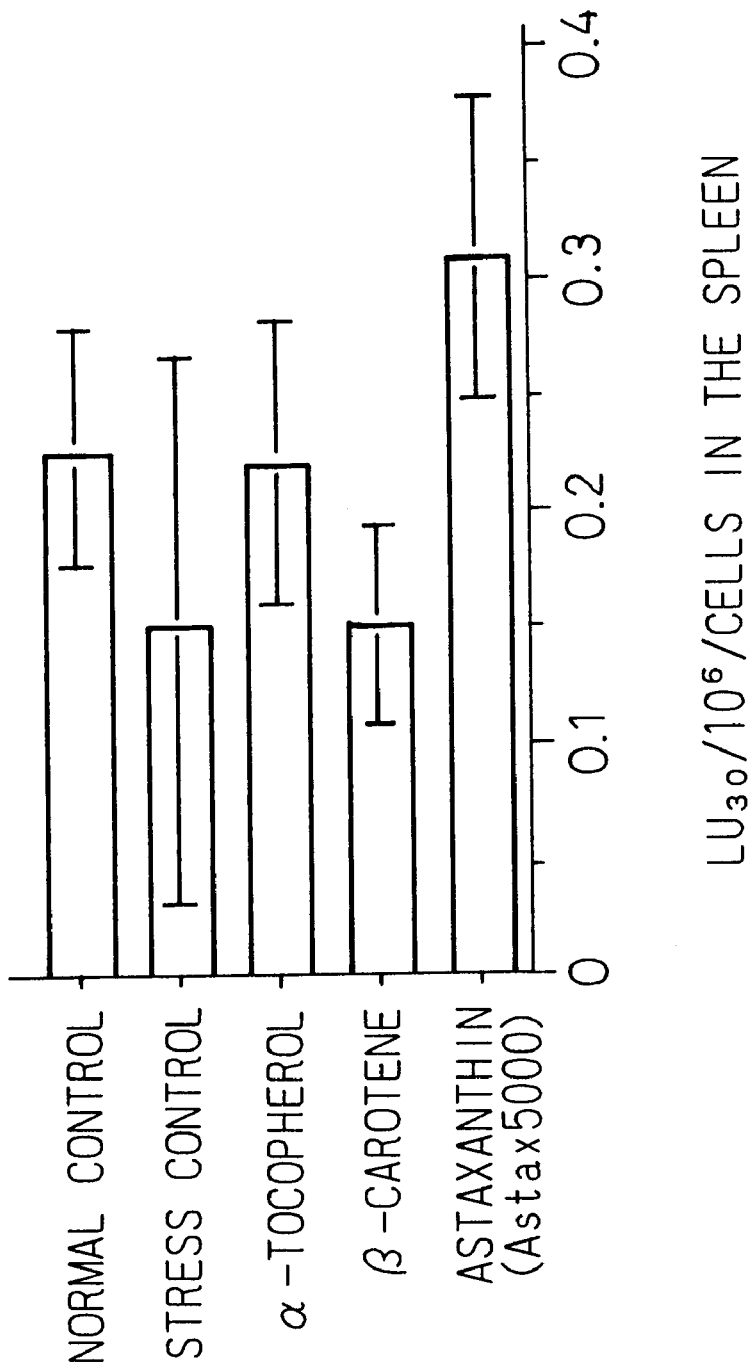
FIG. 3 is a graph showing the improving effect of astaxanthin on decreased NK cell activity caused by stress.

Those results are shown in FIG. 3. Although NK cell activity per spleen lymphocyte decreased due to stress, administration of astaxanthin inhibited the decrease in cell impairment activity of the NK cells, thus confirming that it exhibits an inhibitory effect on decreased immunological function caused by stress.

Example 3

Effect of Restraint Stress on Increased Liver Lipid Peroxides

The livers were excised from those mice sacrificed after 48 hours from the start of restraint of Example 1. The lipid peroxides contained in the liver tissue were determined in the form of the products of reaction with 2-thiobarbituric acid (TBA) in accordance with the method of Uchiyama and Mihara (Uchiyama, et al.: Anal. Biochem. 86, 271).

Namely, 9 volumes of 1.15% cold KCl solution were added to each of the livers excised from each group of mice followed by tephrohomogenization. 0.5 ml of a 5-fold dilution of the homogenate was transferred to a capped Pyrex test tube followed by the addition of 0.3 ml of 1% phosphoric acid and 1.0 ml of 0.67% TEA solution and boiling for 45 minutes after sealing.

Figure 4:
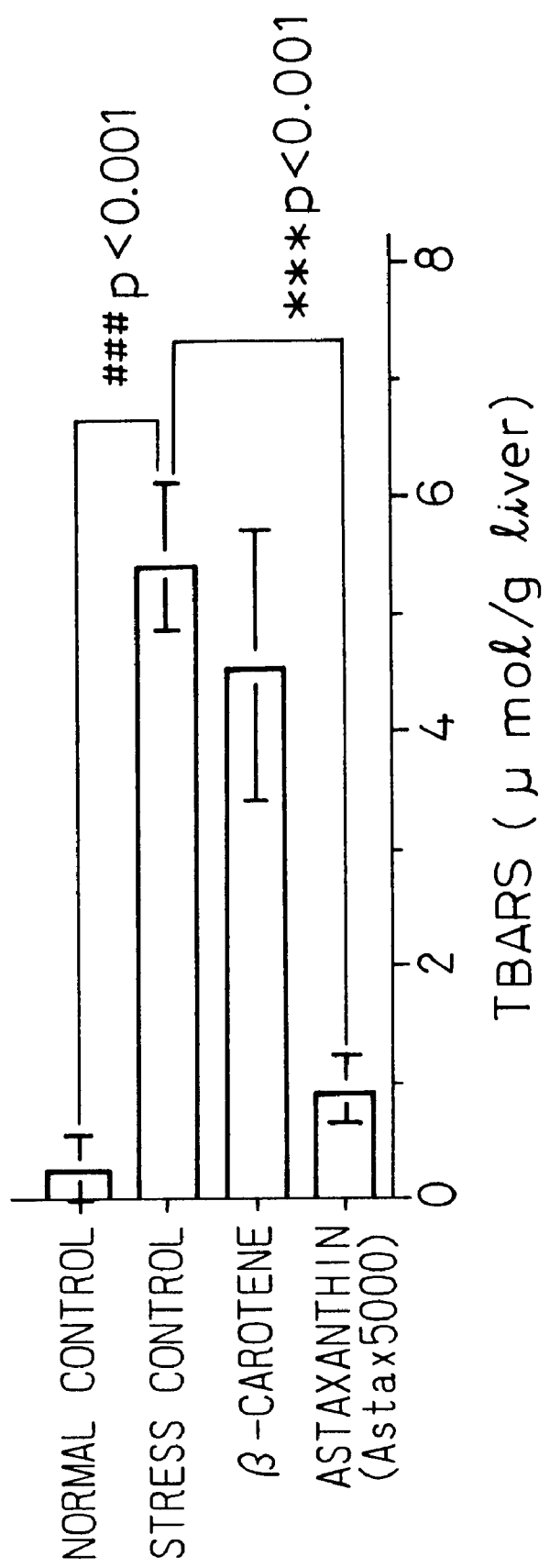
FIG. 4 is a graph showing the suppresive effect of astaxanthin on the formation of lipid peroxide in the liver caused by stress.

After rapid cooling, 4.0 ml of n-butanol were added followed by shaking and centrifugal separation for 10 minutes at 3000 rpm. The absorbance difference (A535–520) in the resulting butanol layer was then measured. The amount of TBA reaction product was calculated using 1,1,3,3-tetraethoxypropane for the standard compound and was expressed as μmoles/g liver tissue wet weight. Those results are shown in FIG. 4. As shown in FIG. 4, although liver lipid peroxide increased significantly due to restraint stress, administration of astaxanthin significantly inhibited this increase, thus confirming that it exhibits an inhibitory effect on decreased liver function caused by stress.

Example 4

Study of the Minimum Effective Dose of the Anti-Stress Effect of Astaxanthin

Astaxanthin (Roche) was dissolved in MCT to astaxanthin concentrations of 0.04 mg/10 ml, 0.2 mg/10 ml, 1.0 mg/10 ml and 5.0 mg/10 ml to prepare the test substance solutions.

Figure 5:
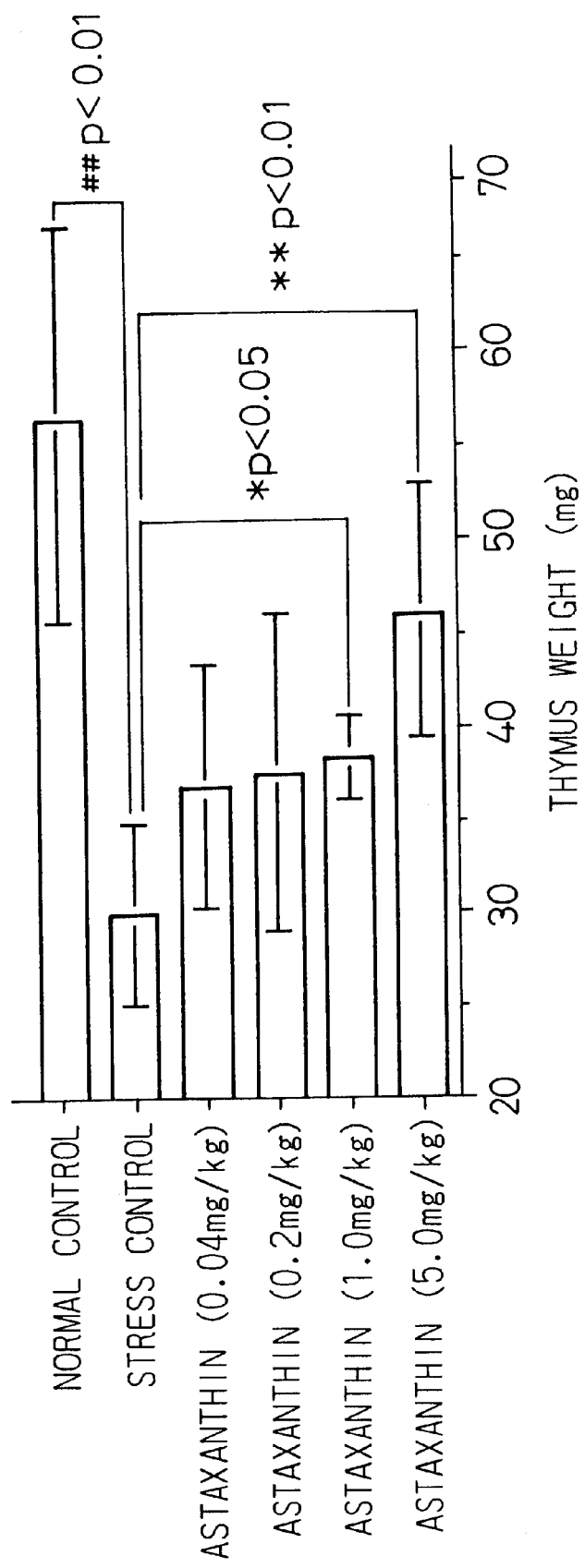
FIG. 5 is a graph showing the weight increasing effect of astaxanthin on decreased thymus weight caused by restraint stress.
Figure 6:
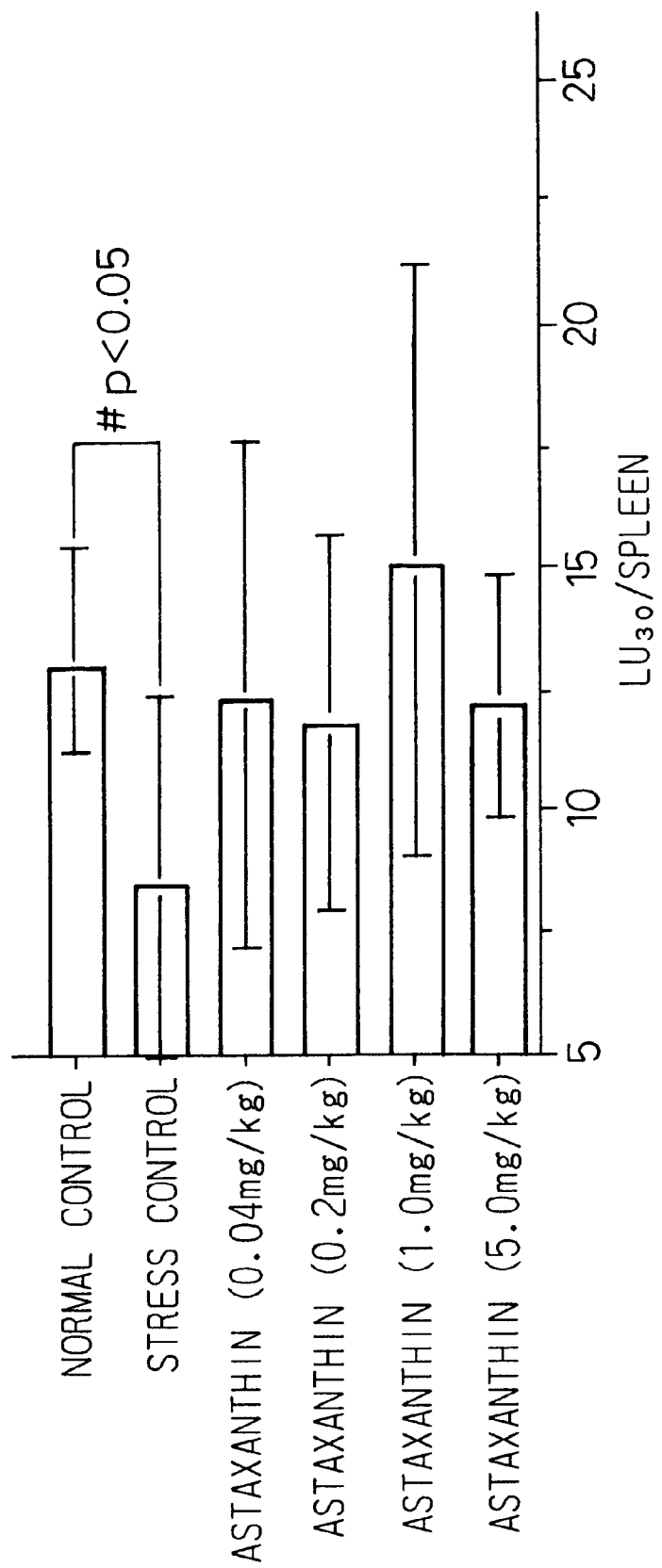
FIG. 6 is a graph showing the improving effect of astaxanthin on decreased NK cell activity of liver origin caused by stress.

Thymus weight and spleen-origin NK cell activity were measured using the same procedures as described in Examples 1 and 2. Those results are shown in FIGS. 5 and 6. Animals of the astaxanthin group exhibited dose-dependent inhibitory effects on significant decreases in thymus weight caused by stress loading, and that effect was significant at doses of 1.0 mg/kg and above. With respect to NK cell activity, an inhibitory trend was observed at doses of 0.04 mg/kg and above on decreased activity caused by stress. These findings suggest that the minimum effective dose of astaxanthin is roughly 1.0 mg/kg.

Example 5

Effect of Restraint Stress on Promotion of Cancer Metastasis 7 week old, male DBA/2 mice were purchased from Japan Clea Co., Ltd., and after housing on a preliminary basis for 1 week in a specific pathogen free (SPF) atmosphere, the animals were used in the experiment at age 8 weeks.

The experimental mice were divided into three groups consisting of a restraint stress non-loaded control group (8 mice), a restraint stress loaded control group (8 mice) and a restraint stress loaded astaxanthin group (9 mice). Astaxanthin was administered orally by gavage three times on the day before restraint, immediately after the start of restraint and the day after the start of restraint at a dose of 1 mg/kg (MCT solution) each. Roche astaxanthin, a synthetic form of astaxanthin, was used for the test substance, while the control groups were orally administered MCT only three times by gavage. Restraint stress loading was performed under the same conditions as Example 1.

Figure 7:
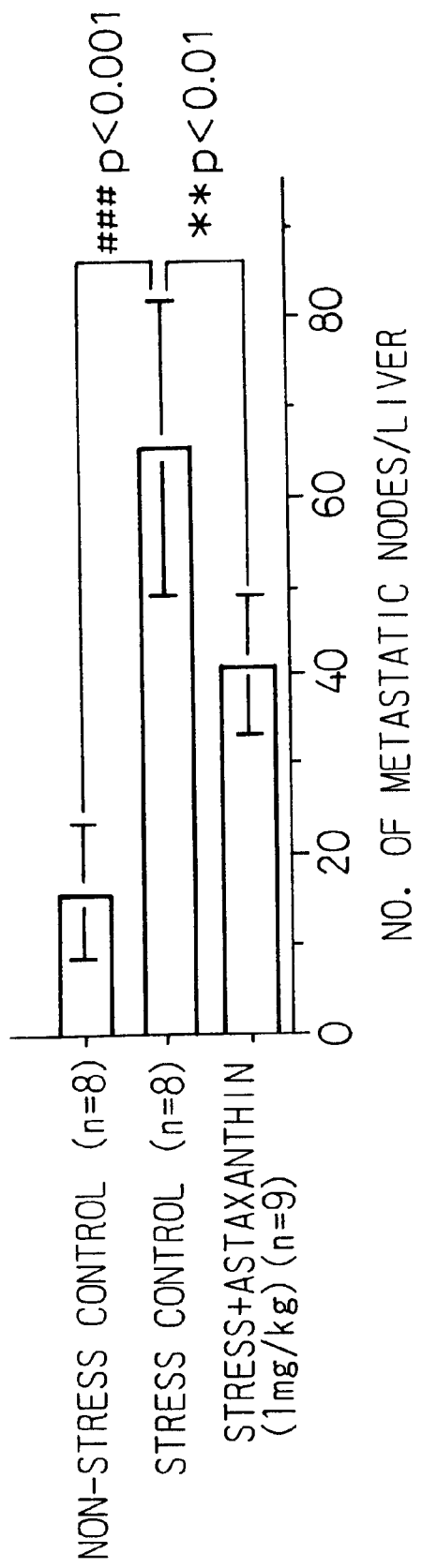
FIG. 7 is a graph showing the inhibitory effect of astaxanthin on increased node metastasis based on a decrease in immunoactivity caused by stress.

Mastocytoma subcultured in the abdominal cavities of DBA/2 mice in this laboratory was used for the P815 mastocytoma (DBA/2 mouse cutaneous mastocytoma). $1 \times 10^4$ cells/animal were transplanted into the caudal vein of each animal. Furthermore, animals of the restraint stress groups were transplanted with mastocytoma 24 hours after the start of stress loading. The liver was excised 16 days after transplantation and after Vaughn's fixation, the number of transplanted nodes on the liver surface was measured. Those results are shown in FIG. 7. As shown in FIG. 7, when a decrease in immunoactivity (NK cell activity, etc.) occurred due to stress loading, metastasis of the transplanted liver cancer was significantly promoted because of this. It was confirmed that administration of astaxanthin caused remarkable inhibition of promotion of cancer metastasis due to decreased immunological function caused by stress.

| Preparation Example 1. Capsules | |
| --- | --- |
| Gelatin | 70.0% |
| Glycerine | 22.9% |
| Methyl paraoxybenzoate | 0.15% |
| Propyl paraoxybenzoate | 0.51% |
| Water | As necessary |
| Total | 100% |

Krill extract oil (containing 3.57% astaxanthin diester and 1.53% astaxanthin monoester) was filled into soft capsules composed of the above-mentioned ingredients in accordance with routine methods to obtain soft capsules weighing 180 mg per capsule.

| Preparation Example 2. Drink | |
| --- | --- |
| Flavoring: | |
| DL-sodium tartrate | 1 g |
| Succinic acid | 0.09 g |
| Sweetener: Liquid sugar | 8 Kg |
| Sourness: Citric acid | 120 g |
| Vitamin: Vitamin C | 100 g |
| Astaxanthin ethylester | 30 g |
| Vitamin E | 300 g |
| Cyclodextrin | 50 g |
| Fragrance | 150 ml |
| Potassium chloride | 10 g |
| Magnesium sulfate | 5 g |

The above-mentioned ingredients were blended followed by the addition of water to bring to a final volume of 100 liters. Approximately 100 ml of this drink is consumed per serving.

| Preparation Example 3. Tonic | |
| --- | --- |
| Flavoring: | |
| DL-sodium tartrate | 1 g |
| Succinic acid | 0.09 g |
| Sweetener: Liquid sugar | 8 Kg |
| Sourness: Citric acid | 120 g |
| Vitamins: | |
| Vitamin C | 100 g |
| Vitamin B1 | 20 g |
| Vitamin B2 | 20 g |
| Vitamin B6 | 20 g |
| Vitamin B12 | 20 g |
| Folic acid | 10 g |
| Nicotinic acid | 20 g |
| Vitamin E | 300 g |
| Cyclodextrin | 50 g |
| Astaxanthin ethylester | 30 g |
| Fragrance | 150 ml |

-continued

Preparation Example 3. Tonic

| Potassium chloride | 10 g |
| Magnesium sulfate | 5 g |

The above-mentioned ingredients were blended followed by the addition of water to bring to a final volume of 100 liters. Approximately 100 ml of this tonic is consumed per serving.

We claim:

1. A method of increasing or recovering thymus lymphocyte- and NK cell-mediated immune response to treat stress in a subject comprising administering astaxanthin and/or an ester thereof to the subject in an amount effective for increasing or recovering thymus lymphocyte- and NK cell-mediated immune response.

2. A method of increasing or recovering thymus lymphocyte- and NK cell-mediated immune response to prevent or alleviate decreased immunological function caused by stress in a subject, comprising administering astaxanthin and/or an ester thereof to the subject in an amount effective for increasing or recovering thymus lymphocyte- and NK cell-mediated immune response.

3. A method of increasing or recoverig thymus lymphocyte- and NK cell-mediated immune response to prevent or alleviate a medical symptom due to decreased immunological function caused by stress in a subject, comprising administering astaxanthin and/or an ester thereof to the subject in an amount effective for increasing or recovering thymus lymphocyte- and NK cell-mediated immune response.

4. A method of increasing or recovering thymus lymphocyte- and NK cell-mediated iimune response to prevent or alleviate fatigue caused by stress in a subject comprising administering astaxanthin and/or an ester thereof to the subject in an amount effective for increasing or recovering thymus lymphocyte- and NK cell-mediated immune response.

5. A method according to claim 1, wherein said astaxanthin and/or its ester is incorporated into a food or drink.

6. A method according to claim 2, wherein said astaxanthin and/or its ester is incorporated into a food or drink.

7. A method according to claim 3, wherein said astaxanthin and/or its ester is incorporated into a food or drink.

8. A method according to claim 3, wherein said medical symptom prevented or alleviated is cancer metastasis or cancer promotion, wherein the cancer promotion is caused by a decrease of thymus lymphocyte- and NK cell-mediated immune response.

9. A method according to claim 5, wherein said astaxanthin and/or its ester is incorporated into a food or drink.

* * * * *